United States Patent [19]
Hempel et al.

[11] Patent Number: 4,678,753
[45] Date of Patent: Jul. 7, 1987

[54] BLOOD-CULTURE FLASK WITH INTEGRATED SUBCULTURE

[75] Inventors: Hans D. Hempel, Mainaschaff; Jürgen Horn, Egelsbach; Wilfried Rothermel, Dietzenbach; Hans H. Sonneborn, Heusenstamm; Michael Becker, Offenbach; Ullrich Müller, Rüsselsheim, all of Fed. Rep. of Germany

[73] Assignee: Biotest-Serum-Institut GmbH, Frankfurt/M, Fed. Rep. of Germany

[21] Appl. No.: 769,908

[22] Filed: Aug. 26, 1985

[30] Foreign Application Priority Data

Aug. 25, 1984 [DE] Fed. Rep. of Germany ... 8425171[U]

[51] Int. Cl.$^4$ ............................................. C12M 1/24
[52] U.S. Cl. .................................... 435/296; 215/227; 215/276; 215/277
[58] Field of Search ............... 435/296; 215/227, 277, 215/276

[56] References Cited

U.S. PATENT DOCUMENTS

| | | | |
|---|---|---|---|
| 3,499,568 | 3/1970 | Riera | 215/276 X |
| 3,589,983 | 6/1971 | Holderith | 435/296 |
| 3,651,926 | 3/1972 | Elfast | 435/296 UX |
| 3,871,545 | 3/1975 | Bereziat | 215/277 X |
| 4,230,231 | 10/1980 | Burnett | 215/277 X |

FOREIGN PATENT DOCUMENTS

| | | |
|---|---|---|
| 1959902 | 7/1970 | Fed. Rep. of Germany . |
| 2806902 | 7/1979 | Fed. Rep. of Germany . |
| 8309876.3 | 12/1983 | Fed. Rep. of Germany . |

OTHER PUBLICATIONS

Castaneda-Ruiz, M., 7/1947, "Castaneda Blutkulturflasche; Kulturtechnik", 1 pg.
Review Article, H. K. Baird et al, "Industrial Applications of Some New Microbial Polysaccharides", Biotechnology, Nov. 1983, pp. 778–783.
Difco Manual, Baco, MacConkey, Agar, "Dehydrated Culture Media", pp. 131–133, 9th ed., 8/1977.

Primary Examiner—Alan Cohan
Attorney, Agent, or Firm—Sprung Horn Kramer & Woods

[57] ABSTRACT

A blood-culture flask with an integrated subculture. It comprises a flask proper that can be filled with a liquid nutrient solution and has a neck with an outside thread, a support that can be coated with a solid culture medium, a resilient stopper with an edge that projects at one end, and a screw cap. The screw cap consists of a bottom that is open above and below and has an inside thread and of a top that is open below. The inside thread is dimensioned so that it can be screwed down over the outside thread on the neck of the flask so that the upper edge of the thread is below the upper edge of the neck when screwed on. The resilient stopper is positioned inside the bottom of the screw cap so that the bottom surface of its resilient projecting edge comes to rest against the offset above the thread when not screwed on and its lower section is dimensioned so that it can be introduced tight into the neck of the flask. The support has two surface that can be coated with a solid culture medium on opposite sides, is fastened to the bottom of the resilient stopper, and extends in use only over part of the height of the flask, and the top of the screw cap is designed so that in assembled state it forces the resilient projecting edge of the stopper tightly against the upper edge of the neck of the flask.

8 Claims, 6 Drawing Figures

BLOOD-CULTURE FLASK WITH INTEGRATED SUBCULTURE

BACKGROUND OF THE INVENTION

The present invention relates to a blood-culture flask 1 with an integrated subculture comprising a flask 2 proper that can be filled with a liquid nutrient solution and has a neck 3 with an outside thread 5, a support 6 that can be coated with a solid culture medium 25, a resilient stopper 7 with an edge that projects at one end, and a screw cap 9.

Detecting the presence of microorganisms in body fluids, especially of bacteria in the blood, by innoculating a liquid nutrient medium with the patient's blood to enrich the nutrient with any pathogens that may be present and then allowing growth on a solid culture medium is generally common.

What are called two-phase blood-culture flasks, in which both culture media are combined into a closed system in one container in order to prevent the otherwise conventional labor-intensive subculturing and avoid the usually inescapable risk of contamination, have been available for a long time for this purpose.

These culture flasks are triangular, rectangular, or hexagonal glass bottles that are filled to about one half or one third with liquid nutrient medium and are coated on one side with a solid nutrient medium. All of the flasks have some sort of air-tight seal that can be penetrated with a hypodermic needle or similar device. They must not be opened during the innoculation. They are described by M. Castaneda-Ruiz in "Practical method for routine blood cultures in brucellosis," *Proc. Soc. Exp. Biol Med.* 64, 114–15 (1947) and are called Castaneda flasks, two-phase Hemoline-Trypcases, or Vacuneda flasks in the literature of various manufacturers.

The solid culture phase in the aforesaid systems always extends down over the total height of one side of the flask into the liquid culture phase and is accordingly always in contact with the liquid phase when the flask is standing erect. The constant contact between the phases results in an exchange of contents, with the liquid nutrient solution becoming cloudy and the color and/or consistency of the layer of solid nutrient altering. This process is especially undesirable when boiled blood agar, which is especially sensitive to lixiviation by the liquid phase, is employed. Although boiled blood agar is an especially practical nutrient agar for blood subcultures, especially for culturing demanding microorganisms, it cannot be employed in the aforesaid closed two-phase systems for the reasons just described.

Although this drawback is admittedly avoided in accordance with German Utility Model No. 8 309 876, by employing a two-phase bottle that has a culture-medium adjunct in the form of a bay-like convexity at the top of one side, so that the solid culture-medium phase located within it is positioned above the level of the liquid nutrient medium to prevent undesired contact between the two phases as long as the flask is maintained erect, it is relatively difficult and expensive to manufacture not only this type of flask but also other types to the extent that they involve concavities and interior ribs to secure the culture medium.

Furthermore, all of these types of culture flasks entail a common drawback in that the solid culture-medium phase cannot be removed subsequent to cultivation of the flask.

German Patent No. 2 806 902 describes a system that consists of two separate containers, with the liquid culture medium in one and the solid nutrient phase in the other. Each container is separate from the other and separately sealed before being used. In use, each container must be opened and, subsequent to innoculation of the liquid culture medium, connected together with a sealing ring, preferably made out of polyethylene. The container with the solid culture medium is at that time relatively higher than the other container. The support for the solid culture medium is a sort of microscope slide.

Although this system does eliminate the drawbacks of constant contact between the solid and liquid phases and of manufacturing expense, it entails still other drawbacks. The necessity of opening both containers subsequent to innoculation involves the risk of secondary contamination.

The necessary opening of the container with the fluid medium allows air into the container and impedes the detection of obligatorily anaerobic pathogens. Nor can capnophilic bacteria, bacteria that depend on carbon dioxide, be detected, because the support with the solid culture medium is located only at the top, whereas the heavy carbon dioxide is present only at the very bottom. Thus the growth of anaerobic and capnophilic pathogens is very unsatisfactory in such a system.

German OS No. 1 959 902 describes a closed two-phase blood-culture flask into which a supporting tray for accommodating solid culture media is inserted and that is completely sealed with a rubber stopper and screw cap.

This is accordingly a closed system that is innoculated while evacuated, that can be cultivated with or without air, and from which the solid culture medium can be removed subsequent to cultivation. The tray is made out of cast resin, glass, or another ceramic material and has a hollow, cylindrical end positioned in the opening in the neck of the bottle, establishing a friction seal. The space inside the cylinder is filled by a resilient stopper with an upper edge that rests against the upper edge of the cylindrical end. The ensemble can be covered with a screw cap. This culture flask, however, entails the drawback that the bottle cannot be sealed 100% tight with a friction seal between the cylindrical end of the supporting tray and the neck of the flask, both of which are made of rigid materials. Nor does the edge of the resilient stopper that projects out at the top suffice to completely seal the bottle, so that air can penetrate into or gas escape from a bottle that has been evacuated or contains a particular gas.

Since the supporting tray extends over the whole height of the flask, this culture flask also has the drawback initially described in relation to known two-phase blood-culture flasks in that the solid culture medium is always in contact with the liquid culture medium when the bottle is erect.

Another disadvantage is that the supporting tray is coated on only one side and, unless the side is divided with partitions, different culture-medium compositions cannot be employed as is necessary for differential microorganism growth. Although the document does describe one embodiment in which the supporting tray is divided into different sections by webs, the areas of the sections are so small that the embodiment is not appropriate for practical applications.

Finally, there is another drawback in that the support, which consists of the tray and cylindrical end, is extremely complicated from an engineering standpoint and hence relatively expensive.

SUMMARY OF THE INVENTION

The object of the present invention is to provide a blood-culture flask that has an integrated subculture and is in the form of a closed system, without, that is, the drawbacks of an open system, such as the risk of secondary contamination and alteration in the atmospheric consistency when the flask has to be opened, and without the drawbacks of the previously known closed systems, a flask, that is, in which the solid and liquid phases are reliably kept separate, from which the solid culture medium can be removed if desired, which can be evacuated, which has a culture-medium support with at least two large enough surfaces that can be coated, in which the culture medium does not come into contact with the nutrient solution even in the upright position, which is simple and inexpensive from an engineering standpoint, which can be completely sealed, and which can be innoculated and cultured in the evacuated state.

This object is attained in that the screw cap 9 for such a culture flask 2 consists of a bottom 10 that is open above and below and has an inside thread 11 and of a top 13 that is open below, in that the inside thread 11 is dimensioned in such a way that it can be screwed down over the outside thread 5 on the neck 3 of the flask in such a way that the upper edge of the thread is below the upper edge 4 of the neck 3 when screwed on, in that a resilient stopper 7 is positioned inside the bottom 10 of the screw cap 9 in such a way that the bottom surface of its resilient projecting edge 8 comes to rest against a flange 12 above the thread when not screwed on and its lower section is dimensioned in such a way that it can be introduced tight into the neck 3 of the flask, in that a support 6 has two surfaces that can be coated with a solid culture medium on opposite sides, is fastened to the bottom of the resilient stopper 7, and extends in use only over some of the height of the flask 2, and in that the top 13 of the screw cap is designed in such a way that in the applied state it forces the resilient projecting edge 8 of the stopper 7 tight against the upper edge 4 of the neck 3 of the flask.

An essential element of the blood-culture flask in accordance with the invention is the sealing system with integrated culture-medium supports, the interplay, in other words, between the bottom of the screw cap, the top of the screw cap, the resilient stopper with the culture-medium support attached to it, and the neck of the flask. The bottom of the screw cap, which is in the form of a hollow cylinder has in its lower section an inside thread that screws over the outside thread on the neck of the flask. The stopper has a resilient edge that projects at the top, something called a "hat." Since the diameter of the hat is the same as the inside diameter of the unthreaded bottom of the screw cap, the bottom surface of its resilient projecting end or hat rests against a flange above the upper edge of the inside thread. The diameter of the lower part of the stopper is thicker enough than the inside diameter of the neck of the flask to make it possible to force it tightly into the neck. The stopper can be make for example out of natural or synthetic rubber or a resilient plastic.

The top of the screw cap can be fastened, preferably screwed, firmly to the bottom of the cap and is shaped to exert pressure on the stopper when applied. The screw connection can in a practical way either be established with an outside thread on the top of the screw cap over a matching inside thread on the upper part of the bottom of the screw cap, or the top of the screw cap can over-lap the bottom of the screw cap and screw on by means of an inside thread over an outside thread on the bottom of the screw cap.

In so doing, it is essential for the flange above the upper edge of the inside thread on the bottom of the screw cap to come to rest below the upper edge of the neck of the flask in the screwed-on state. The resilient stopper will now of necessity rest against the upper edge of the neck. The pressure of the top of the screw cap on the stopper forces the latter through the loose space between the upper edge of the neck of the flask and said flange and accordingly constitutes a completely air- and gas-tight seal.

A distance of 0.5 mm between said flange and the upper edge of the neck of the flask is sufficient to attain this effect.

In one preferred embodiment of the invention, the neck of the flask has a flange below its outside thread that functions as a stop for the bottom of the screw cap. This makes it possible to establish the distance between the upper edge of the bottle and the upper edge of the thread inside the bottom of the screw cap.

Another advantage of the system in accordance with the invention is that the resilient stopper, which rests against the offset above the upper edge of the inside thread, will lift when the cap is unscrewed, meaning that it can easily be removed along with the culture-medium support without being touched.

In addition to forcing down the resilient stopper, the top of the screw cap also covers up the area where the needle is inserted through the stopper and keeps it sterile.

Appropriate culture-medium supports are flat plates of the type called dip slides or microorganism indicators. The support must be just long enough to extend over part of the height of the flask. It must always terminate above the level of the nutrient fluid inside the flask. There must be enough empty space between the fluid level and the end of the support to eliminate contact between the solid and liquid culture media if the flask is shaken during shipping. A support of this type is intended to be coated on each side with solid culture medium in such a way as to provide two selective phases. If more than two phases are desired, one or both sides of the support can be partitioned longitudinally or transversely.

Especially practical is a support with a smooth surface to provide no points of attack for blistering when the flask is evacuated and with retainer surfaces that cut across the culture medium to prevent it from sliding off when wet. The retainer surfaces can be applied on all four sides of the support, on only one narrow side and both longitudinal sides, or only on both longitudinal sides. They can be continuous or interrupted.

The solid culture media can be any of the media conventional for this purpose, agar for example. Especially satisfactory are agar media treated with Gellan gum, a polysaccharide. Outstanding is Gellan gum with a low acetyl content, especially when it is very transparent, like the commercially available brand Gelrite ® (cf. J. K. Baird et al., "Industrial applications of some new microbial polysaccharides," *Biotechnology*, November, 1983, 778–83). Culture media containing for example 10 g of agar and 4 g of Gelrite per liter have turned out to adhere very well to supports employed in accordance with the invention, whereas 19 g per liter of pure agar are necessary for satisfactory adhesion.

No gaps form along the undercuts in the retainer surfaces. This type of culture medium also turned out to be more dimensionally stable on the support inside the blood-culture flask, especially while the flask is being evacuated. Finally, improved growth (larger colonies) was observed for some microorganisms that with pure agar.

If the liquid culture medium, however, unintentionally come into contact with the support, it can be eluted out if the solid culture medium contains lower-molecular substances. Although the solid culture medium, especially the type just described, retains its adhesion, it will lose its typical properties, so that for example the coliform microorganisms on a MacConkey will become atypical because the bile salt and crystal violet are eluted out. To prevent this bleeding out of the lower-molecular substances and ensure typical growth, the use of a combination culture medium is recommended, with a layer of McConkey that has Gellan gum, preferably Gerite ®, added to it and that has about 2 to 8 times more lower-molecular substances like bile salts and crystal violet than usual being applied to the support and then coated with normal agar or McConkey conventional composition.

It is practical for the bottom of the support to have a drip point to allow excess nutrient solution to drip off better subsequent to wetting.

Especially practical means of fastening the support to the resilient stopper one or preferably two rod-like connections on one narrow side of the support that extend into matching holes in the stopper. To ensure an especially secure attachment, the rods should have thicker sections and the holes should be undercut. The rods can have any desired cross-section: a cross, a star, a circle, etc.

The support can be made out of any moldable material that is inert in relation to the culture media. It will preferably be made out of a plastic that is inert in relation to both the solid and the liquid culture medium.

The flask in itself can be any type of blood-culture flask. It can be round or polygonal and made out of glass or transparent plastic. It is, however, preferably made out of glass, which is less permeable to gas than is plastic. It should be large enough for the volume of nutrient solution normally employed for blood cultures, that is 40-100 m , to take up as near as possible no more than half the height of the flask in order to allow enough empty space for the culture-medium support. The neck of the flask must be round and wide enough to allow introduction of the support and is provided with an outside thread, a normal DIN thread in practical terms.

The fact that the flask in accordance with the invention can be innoculated and cultured in the evacuated state makes it especially appropriate for anaerobic pathogens. Any residual air or gas can remain in the system if desirable.

Some preferred embodiments of the invention will now be described with reference to the attached drawings, wherein

DETAILED DESCRIPTION OF THE PREFERRED EMBODIMENTS

Figure 1:
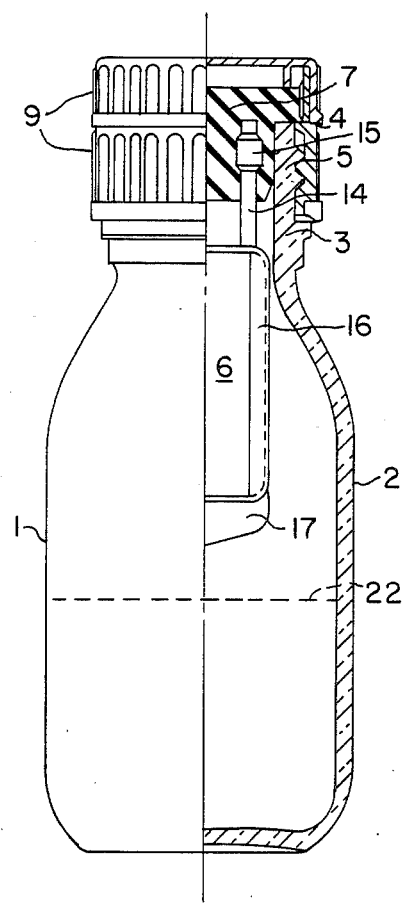
FIG. 1 is a front view, partly in section, of a flask with an integrated support.

FIG. 1 shows a blood-culture flask 1 consisting of a flask 2 proper with a neck 3 that has an upper edge 4 and an outside thread 5. A support 6 with retainer surfaces 16, a drip point 17, and connections 14 that have thicker sections 15 is inserted into a resilient stopper 7. The fluid level 22 is somewhat below support 6. The design of neck 3 and of a screw cap 9 is illustrated on a larger scale in FIG. 2 and will be described with reference thereto.

Figure 2:
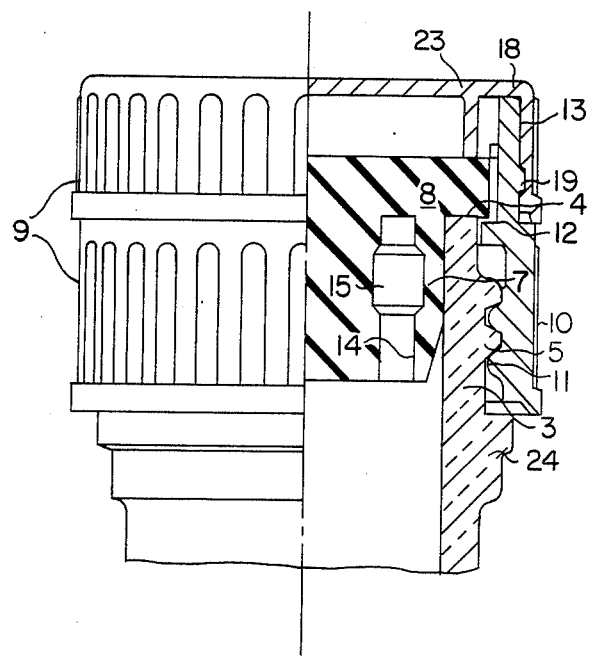
FIG. 2 is a front view, partly in section, of the sealing system in conjunction with the neck of the flask.

The bottom 10 of screw cap 9 in FIG. 2 has an inside thread 11 and is screwed over the thread 5 on the outside of the neck 3 of flask 2. A flange 12 above the upper edge of inside thread 11 is positioned below the upper edge 4 of neck 3. The bottom surface of the projecting resilient edge 8 of resilent stopper 7 rests on the upper edge 4 of neck 3. In the screwed-on state the top 13 of screw cap 9 forces projecting resilient edge 8 into the gap 23 between flange 12 and the upper edge 4 of neck 3, producing a hermetic seal. The two parts of screw cap 9 are screwed together by means of a thread 19 inside its top 13 and of a somewhat set-back thread 18 outside its bottom.

Below the thread 5 on the outside of the neck 3 of flask 2 is a flange 24 that functions as a stop for the screwed-on bottom 10 of screw cap 9. Connections 14 for support 6 and with thicker sections 15 are inserted in resilient stopper 7.

Figure 3:
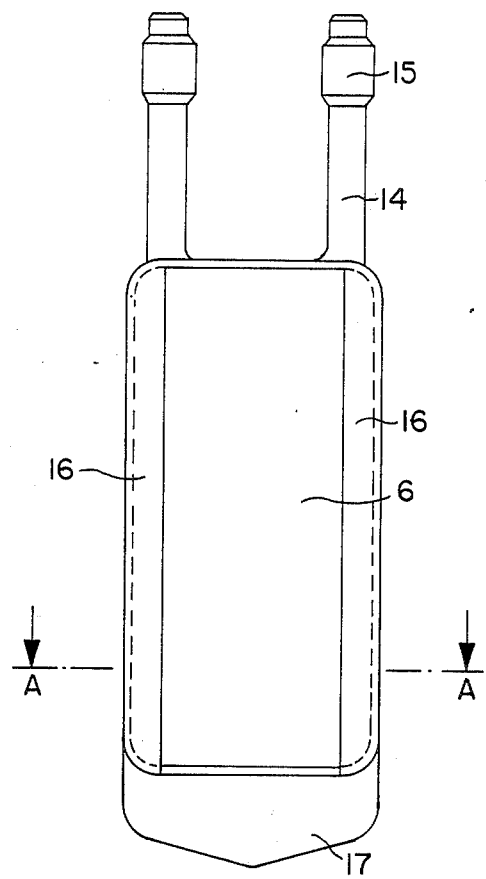
FIG. 3 is a front view of an upright projection of a support.

FIG. 3 shows the support 6 with its retainer surfaces 16, rod-like connections 14 and thicker sections 15 for insertion into a resilient stopper, and a drip point 17.

Figure 4:
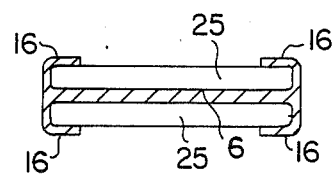
FIG. 4 is a section through the support on line A—A of FIG. 3.

FIG. 4 is a section through a support 6 with retainer surfaces 16 and a solid culture medium 25 on each side.

Figure 6:
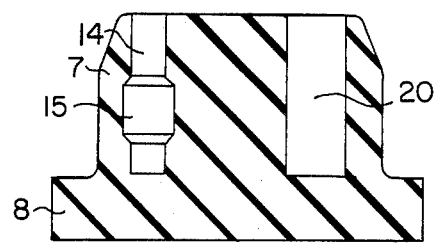
FIG. 6 is a vertical section through the resilient stopper showing the rod-like support connections, taken along line B—B of FIG. 5.

FIG. 6 shows rod-like connections 14 with their thicker sections 15 as inserted in stopper 7. Also evident are the resilient projecting edge 8 of stopper 7 and bores 20 for receiving the connections.

Figure 5:
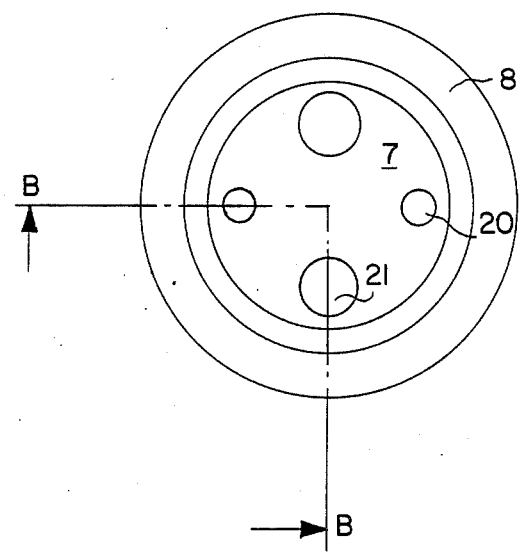
FIG. 5 is a top view of the resilient stopper.

The top view in FIG. 5 shows resilient stopper 7 with its resilient projecting edge 8, bores 20 for receiving support 6, and marks 21 indicating where to insert a needle.

It is understood that the specification and examples are illustrative but not limitative of the present invention and that other embodiments within the spirit and scope of the invention will suggest themselves to those skilled in the art.

What is claimed is:

1. A blood-culture flask with an integrated subculture comprising a flask 2 that can be filled with a liquid nutrient solution and has a neck 3 with an outside thread 5 and an upper edge 4, a support 6 for a solid culture medium, a resilient stopper 7 with an edge 8 that projects at one end, and a screw cap 9 comprising a bottom 10 that is open above and below and has an inside thread 11 with an inside flange 12 above the inside thread and a top 13 that is open below, the inside thread 11 being dimensioned so that it can be screwed down over the outside thread 5 on the neck 3 of the flask in such a way that the flange 12 is above the outside thread 5 and is below the upper edge 4 of the neck 3 when screwed on, the resilient stopper 7 being positioned inside the botton 1 of the screw cap 9 so that the bottom surface of its resilient projecting edge 8 comes to rest against the flange 12 above the outside thread when not screwed on and its lower section is dimensioned so that it can be introduced tightly into the neck 3 of the flask, the support 6 having two surfaces that can be coated with a solid culture medium on opposite sides and which are provided with retainer surfaces 16 on at least the two longitudinal sides, overlapping the solid culture medium, the support being fastened to the bottom of the resilient stopper 7, and extending in use only over part of the height of the flask 2, the top 13 of the screw cap in assembled state forcing the resilient projecting edge 8 of the stopper 7 tightly against the upper edge 4 of the neck 3 of the flask.

2. A blood-culture flask according to claim 1, wherein the neck 3 of the flask 2 has a flange 24 below its outside thread 5 that functions as a stop for the bottom 10 of the screw cap 9.

3. A blood-culture flask according claim 1, wherein the support 6 at its upper edge has at least one rod-like connection 14 with a thicker section 15, and the resilient stopper 7 is provided in its bottom surface with a matching bore 20, into which the connections 14 are inserted.

4. A blood-culture falsk according to claim 1, wherein the support 6 has a smooth surface.

5. A blood-culture flask according to claim 1, wherein the support 6 has a drip point 17.

6. A blood-culture flask according to claim 1, wherein the support 6 carries a solid culture medium 25 containing Gellan gum.

7. A blood-culture flask according to claim 6, wherein the solid culture medium 25 has an initial layer of McConkey that has Gellan gum added to it and that has about 2 to 8 times more lower-molecular substances than usual, and a coating layer of normal agar and/or McConkey of conventional composition.

8. A blood-culture flask according to claim 7, wherein the neck 3 of the flask 2 has a flange 24 below its outside thread 5 that functions as a stop for the bottom 10 of the screw cap 9, the support 6 has a smooth surface and a drip point and at its upper edge has at least one rod-like connection 14 with a thicker section 15, and the resilient stopper 7 is provided in its bottom surface with a matching bore 20, into which the connections 14 are inserted, and the surfaces of the support 6 have retainer surfaces 16 on at least the two longitudinal sides.

* * * * *

UNITED STATES PATENT AND TRADEMARK OFFICE
CERTIFICATE OF CORRECTION

PATENT NO. : 4,678,753
DATED : July 7, 1987
INVENTOR(S) : Hans D. Hempel, et al.

It is certified that error appears in the above-identified patent and that said Letters Patent is hereby corrected as shown below:

Col. 5, line 50     Delete "m" and substitute --$m_-$--

Col. 7, line 6      Delete "1" and substitute --10--

Signed and Sealed this

Fifth Day of April, 1988

Attest:

DONALD J. QUIGG

Attesting Officer          Commissioner of Patents and Trademarks